United States Patent
Mrvica et al.

(10) Patent No.: US 9,017,790 B2
(45) Date of Patent: Apr. 28, 2015

(54) ABSORBENT SHEET PRODUCTS AND METHOD FOR FOLDING SAME

(75) Inventors: Maté Mrvica, Pierrefonds (CA); Nathalie Comeau, Candiac (CA); Serge Leroux, Brownsburg-Chatam (CA); Gino Ringuette, Saint-Catherine (CA); Svetlana Visnepolschi, West Bloomfield, MI (US); Vladimir Proseanic, West Bloomfield, MI (US)

(73) Assignee: Cascades Canada ULC, Montreal, Quebec (CA)

( * ) Notice: Subject to any disclaimer, the term of this patent is extended or adjusted under 35 U.S.C. 154(b) by 191 days.

(21) Appl. No.: 13/411,222

(22) Filed: Mar. 2, 2012

(65) Prior Publication Data

US 2012/0225244 A1 Sep. 6, 2012

Related U.S. Application Data

(60) Provisional application No. 61/448,219, filed on Mar. 2, 2011.

(51) Int. Cl.
*A47K 10/16* (2006.01)
*A61F 13/15* (2006.01)
*B65H 45/24* (2006.01)

(52) U.S. Cl.
CPC .......... *A61F 13/15747* (2013.01); *B65H 45/24* (2013.01); *B65H 2701/1924* (2013.01)

(58) Field of Classification Search
CPC ..................................................... A47K 10/16
USPC ..................... 428/126, 130; 221/48; 206/494
See application file for complete search history.

(56) References Cited

U.S. PATENT DOCUMENTS

| | | |
|---|---|---|
| 1,141,395 A | 6/1915 | Johnston et al. |
| 1,158,547 A | 11/1915 | Parsons |
| 1,158,548 A | 11/1915 | Parsons |
| 1,158,549 A | 11/1915 | Parsons |
| 1,158,550 A | 11/1915 | Parsons |
| 1,177,466 A | 3/1916 | Winter |
| 1,222,261 A | 4/1917 | Brown et al. |
| 1,228,400 A | 6/1917 | Brown et al. |
| 1,256,334 A | 2/1918 | Lazar |
| 1,273,609 A | 7/1918 | Hitchcock |
| 1,307,443 A | 6/1919 | Irwin |

(Continued)

FOREIGN PATENT DOCUMENTS

| | | |
|---|---|---|
| EP | 0286538 A1 | 10/1988 |
| EP | 0980841 A2 | 2/2000 |

(Continued)

*Primary Examiner* — Alexander Thomas
(74) *Attorney, Agent, or Firm* — K&L Gates LLP

(57) ABSTRACT

A stack of interfolded absorbent sheet products comprising a plurality of absorbent sheets and a method of folding and stacking the same. Each one of the absorbent sheets is folded twice about a first axis to define two inwardly folded inner panels and at least once about a second axis to define at least two outer panels sandwiching the inner panels therebetween. The second axis is substantially perpendicular to the first axis, Each of the absorbent sheet products comprises at least one outer panel at least partially sandwiched between a pair of outer panels of an adjacent one of the absorbent sheet products of the stack. Each one of the absorbent sheet products is entirely detached from all other absorbent sheet products of the stack.

30 Claims, 8 Drawing Sheets

(56) References Cited

U.S. PATENT DOCUMENTS

| | | |
|---|---|---|
| 1,369,930 A | 3/1921 | McCorkindale |
| 1,378,063 A | 5/1921 | Swick |
| 1,387,572 A | 8/1921 | Weinberger |
| 1,430,709 A | 10/1922 | Wheeler |
| 1,499,926 A | 7/1924 | Hunt |
| 1,501,662 A | 7/1924 | Horwitt |
| 1,600,837 A | 9/1926 | Melker |
| 1,618,711 A | 2/1927 | Hunt |
| 1,642,487 A | 9/1927 | Christman |
| 1,645,189 A | 10/1927 | Ek |
| 1,653,908 A | 12/1927 | Hunt |
| 1,663,391 A | 3/1928 | Shaffer et al. |
| 1,673,763 A | 6/1928 | Flather |
| 1,675,700 A | 7/1928 | Fairchild |
| 1,681,611 A | 8/1928 | Hansen |
| 1,681,639 A | 8/1928 | Hansen |
| 1,683,335 A | 9/1928 | Christman |
| 1,698,823 A | 1/1929 | Rasmussen |
| 1,706,166 A | 3/1929 | Hunt |
| 1,706,220 A | 3/1929 | Fairchild |
| 1,707,581 A | 4/1929 | Shaffer |
| 1,713,000 A | 5/1929 | Magill |
| 1,718,776 A | 6/1929 | Christman |
| 1,727,064 A | 9/1929 | Joseph |
| 1,731,292 A | 10/1929 | Campbell |
| 1,767,859 A | 6/1930 | Shaffer |
| 1,874,850 A | 8/1932 | Daniels |
| 1,878,866 A | 9/1932 | Veck |
| 1,880,345 A | 10/1932 | Gardner |
| 1,911,548 A | 5/1933 | Campbell |
| 1,962,762 A | 6/1934 | Campbell |
| 1,980,059 A | 11/1934 | Housen |
| 1,996,307 A | 4/1935 | Shapiro |
| 2,002,691 A | 5/1935 | Cofrin |
| 2,009,464 A | 7/1935 | Winter |
| 2,027,258 A | 1/1936 | Winter et al. |
| 2,050,030 A | 8/1936 | Winter |
| 2,071,926 A | 2/1937 | Geerlings |
| 2,082,731 A | 6/1937 | Broeren |
| 2,093,724 A | 9/1937 | Horwitt |
| 2,118,472 A | 5/1938 | Morris |
| 2,118,473 A | 5/1938 | Morris |
| 2,125,618 A | 8/1938 | Nystrand |
| 2,138,425 A | 11/1938 | Morris |
| 2,244,630 A | 6/1941 | Metternich |
| 2,260,488 A | 10/1941 | Shapiro |
| 2,477,223 A | 7/1949 | West |
| 3,007,605 A | 11/1961 | Donovan |
| 3,043,472 A | 7/1962 | Nemoede |
| 3,047,141 A | 7/1962 | Burns |
| 3,087,605 A | 4/1963 | Kester |
| 3,119,516 A | 1/1964 | Donovan |
| 3,490,645 A | 1/1970 | Glass et al. |
| 3,499,575 A | 3/1970 | Rockefeller |
| 3,814,100 A | 6/1974 | Nystrand et al. |
| 3,828,989 A | 8/1974 | Heater |
| 4,181,225 A | 1/1980 | Spiegelberg |
| 4,638,921 A | 1/1987 | Sigl et al. |
| 4,785,970 A | 11/1988 | Engelmayer |
| 4,859,518 A | 8/1989 | Schutz |
| 5,118,554 A | 6/1992 | Chan et al. |
| 5,332,118 A | 7/1994 | Muckenfuhs |
| 5,565,258 A | 10/1996 | McConnell et al. |
| 5,577,612 A | 11/1996 | Chesson et al. |
| 5,607,754 A | 3/1997 | Giles et al. |
| 5,736,224 A | 4/1998 | Dodge |
| 5,761,761 A | 6/1998 | An |
| 5,853,845 A | 12/1998 | McConnell et al. |
| 5,964,351 A | 10/1999 | Zander |
| RE36,395 E | 11/1999 | McDonald |
| 5,992,682 A | 11/1999 | Loppnow et al. |
| 6,012,572 A | 1/2000 | Heathcock et al. |
| 6,030,331 A | 2/2000 | Zander |
| 6,045,002 A | 4/2000 | Wierschke |
| 6,090,467 A | 7/2000 | Yip |
| 6,109,430 A | 8/2000 | Bando et al. |
| 6,168,848 B1 | 1/2001 | Heath |
| 6,196,390 B1 | 3/2001 | Bando |
| 6,202,845 B1 | 3/2001 | Hill |
| 6,213,344 B1 | 4/2001 | Hill |
| 6,213,345 B1 | 4/2001 | Plank |
| 6,238,328 B1 | 5/2001 | Loppnow et al. |
| 6,286,712 B1 | 9/2001 | Craig et al. |
| 6,296,144 B1 | 10/2001 | Tanaka et al. |
| 6,306,480 B1 | 10/2001 | Yardley et al. |
| 6,543,643 B2 | 4/2003 | Iida et al. |
| 6,550,634 B1 | 4/2003 | Alegre De Miquel et al. |
| 6,554,134 B1 | 4/2003 | Guibert |
| 6,595,386 B2 | 7/2003 | Vogel et al. |
| 6,602,575 B2 | 8/2003 | Lefevre Du Grosriez et al. |
| 6,623,833 B2 | 9/2003 | Chan |
| 6,641,894 B2 | 11/2003 | Bando |
| 6,644,499 B2 | 11/2003 | Tramontina |
| 6,644,501 B2 | 11/2003 | Lida |
| 6,685,050 B2 | 2/2004 | Schmidt et al. |
| 6,745,917 B2 | 6/2004 | Koyama et al. |
| 6,753,058 B2 | 6/2004 | Månsson |
| 6,848,595 B2 | 2/2005 | Lange et al. |
| 6,960,349 B2 | 11/2005 | Shantz et al. |
| 6,964,349 B2 | 11/2005 | Sears et al. |
| 6,988,635 B2 | 1/2006 | Hochtritt et al. |
| 7,097,896 B2 | 8/2006 | Merrill |
| 7,100,769 B2 | 9/2006 | Tourre et al. |
| 7,204,390 B2 | 4/2007 | Widlund |
| 7,211,311 B2 | 5/2007 | McDonald |
| 7,322,489 B2 | 1/2008 | Long |
| 7,465,266 B2 | 12/2008 | Lange et al. |
| 7,568,594 B2 | 8/2009 | Long |
| 7,571,832 B2 | 8/2009 | Mark et al. |
| 7,611,765 B2 | 11/2009 | Hochtritt et al. |
| 7,837,057 B2 | 11/2010 | Zeiron |
| 7,867,362 B2 | 1/2011 | Allen et al. |
| 7,939,159 B2 | 5/2011 | Hochtritt et al. |
| 8,083,097 B2 | 12/2011 | Kaufman |
| 8,133,569 B2 | 3/2012 | Penfield |
| 8,393,496 B2 | 3/2013 | Bandoh et al. |
| 8,597,761 B2 | 12/2013 | Formon et al. |
| 2002/0068142 A1 | 6/2002 | Baroni et al. |
| 2003/0057223 A1 | 3/2003 | Vogel et al. |
| 2003/0183644 A1 | 10/2003 | Sarnoff et al. |
| 2004/0020936 A1 | 2/2004 | Guillemette et al. |
| 2005/0061827 A1 | 3/2005 | Yardley et al. |
| 2005/0079310 A1 | 4/2005 | Germain |
| 2005/0124960 A1 | 6/2005 | Ruman |
| 2005/0227039 A1 | 10/2005 | Wunderlich |
| 2006/0068162 A1 | 3/2006 | Merrill |
| 2006/0102643 A1 | 5/2006 | Kaufman |
| 2007/0034534 A1 | 2/2007 | VanBuren |
| 2007/0062967 A1 | 3/2007 | Zaidman et al. |
| 2008/0308446 A1 | 12/2008 | Ingram |
| 2010/0104799 A1 | 4/2010 | Wunderlich |

FOREIGN PATENT DOCUMENTS

| | | |
|---|---|---|
| EP | 1127830 B1 | 8/2001 |
| WO | 2008069709 A1 | 6/2008 |
| WO | 2008069709 A8 | 5/2009 |

ABSORBENT SHEET PRODUCTS AND METHOD FOR FOLDING SAME

CROSS-REFERENCE TO RELATED APPLICATIONS

This application claims priority under 35 USC §119(e) of U.S. provisional patent application 61/448,219 filed on Mar. 2, 2011, the specification of which is hereby incorporated by reference.

FIELD OF THE INVENTION

The present invention relates to the field of absorbent sheet products. More particularly, it relates to an absorbent sheet product, a method of folding and stacking absorbent sheets and a stack of absorbent sheet products.

BACKGROUND

Folded absorbent sheet products commonly found on the market, which are manufactured to be released via a dispenser, are mostly single folded sheets or of the type commonly referred to as "half-folded" tissues. The limited thickness and volume of such products often leads to a limited absorbency of the tissue and requires the product to be subsequently folded or crumpled by the user in order to achieve the desired absorbency or softness. As a result, users often take more than one single folded tissue at a time, assessing beforehand that their absorbing ability, and corresponding overall quality, is comparatively low. In such a case the use of single folded tissues leads to excessive waste of the product.

In view of the above, there is a need for an improved absorbent sheet product, a method of folding and stacking absorbent sheets and a stack of the absorbent sheet product which would be able to overcome or at least minimize some of the above-discussed prior art concerns.

SUMMARY

It is therefore an aim of the present invention to address the above mentioned issues.

According to a first general aspect, there is provided a stack of interfolded absorbent sheet products. The stack comprises a plurality of absorbent sheets having an inner face and an opposed outer face. Each of the absorbent sheets comprises a first folding edge and a second folding edge extending substantially parallel to one another and defining respectively a first inner panel and a second inner panel. Each of the absorbent sheets is folded inwardly along the first and second folding edges towards the inner face. Each of the absorbent sheets also comprises a third folding edge extending substantially perpendicular to the first and second folding edges and defining a first outer panel and a second outer panel. Each of the absorbent sheets is folded along the third folding edge such that the first and the second inner panels are inwardly facing. Moreover, at least one of the first and the second outer panels is at least partially inserted between the first and the second outer panels of an adjacent one of the absorbent sheet products of the stack.

According to another aspect, there is also provided a stack of interfolded absorbent sheet products comprising a plurality of absorbent sheets. Each one of the absorbent sheets is folded twice about a first axis to define two inwardly folded inner panels and at least once about a second axis to define at least two outer panels sandwiching the inner panels therebetween. The second axis is substantially perpendicular to the first axis. Each of the absorbent sheet products comprises at least one outer panel at least partially sandwiched between a pair of outer panels of an adjacent one of the absorbent sheet products of the stack. Each one of the absorbent sheet products is entirely detached from all other absorbent sheet products of the stack.

According to yet another aspect, there is also provided a method of stacking a plurality of absorbent sheet products into a stack. The method comprises, for each of the absorbent sheet products of the stack, firstly, folding an absorbent sheet inwardly along a first folding line to form a first inner panel; secondly, folding the absorbent sheet inwardly along a second folding line substantially parallel to the first folding line to form a second inner panel; thirdly folding the absorbent sheet along a third folding line substantially perpendicular to the first and second folding lines to form a first outer panel and a second outer panel, sandwiching the first and second inner panels therebetween, to obtain one of the absorbent sheet products; and finally, inserting at least a section of at least one of the first and the second outer panels of each one of the absorbent sheet products between the first and second outer panels of an adjacent one of absorbent sheet products of the stack.

In an embodiment, the absorbent sheet is folded along the first and the second folding lines concurrently. In an alternative embodiment, the absorbent sheet is folded along the first and the second folding lines sequentially.

In alternative embodiments, the inner panels can be configured to have several configurations, such as, without being limitative, a spaced apart configuration, a partially overlapping configuration or a completely overlapping configuration.

In alternative embodiments, the outer panels can be configured such that their lengths are either similar or different.

In alternative embodiments, a fourth folding edge substantially parallel to the third folding edge may be provided to form a third outer panel.

BRIEF DESCRIPTION OF THE DRAWINGS

Other objects, advantages and features of the present invention will become more apparent upon reading the following non-restrictive description of embodiments thereof, given for the purpose of exemplification only, with reference to the accompanying drawings in which.

DETAILED DESCRIPTION OF EMBODIMENTS

In the following description, the same numerical references refer to similar elements. The embodiments, geometrical configurations, materials mentioned and/or dimensions shown in the figures or described in the present description are embodiments only, given solely for exemplification purposes.

Moreover, although the embodiments of folded absorbent sheet products, method of folding and stacking the same, and stack of the absorbent sheet product consist of certain geometrical configurations as explained and illustrated herein, not all of the components and geometries are essential to the invention and thus should not be taken in their restrictive sense. It is to be understood, as also apparent to a person skilled in the art, that other suitable geometrical configurations may be used for the absorbent sheet product, as will be briefly explained herein and as can be easily inferred herefrom by a person skilled in the art. Moreover, it will be appreciated that positional descriptions such as "top", "bottom", "above", "below", "left", "right" and the like should, unless otherwise indicated, be taken in the context of the figures and should not be considered limiting.

In the context of the present document, the term "absorbent sheet" should be understood to mean any absorbent product provided in the form of a sheet such as, without being limitative, facial tissue, towels, napkins, hankies, wet wipes, paper napkins, or the like, and provided with or without printed or embossed pattern. The type of material used for the absorbent sheet should be understood to comprise any type of predominantly cellulosic material. However, the term "absorbent sheet" is not limited to paper products such as paper napkins and towels, but can also comprise absorbent nonwoven materials not normally classed as papers or tissues. These nonwoven materials can include pure and hybrid nonwovens webs with similar properties to those of tissue paper. These nonwoven webs can be based for instance on nonwoven or airlaid materials containing low amounts of synthetic fibers, binders, wet strength agents and the like. The absorbent sheet can have a printed pattern or an embossed pattern on one or both faces as it is known in the art.

Similarly, the term "absorbent sheet product" refers to an absorbent sheet in its folded configuration, according to the different embodiments and variants described below. In other words, the term "absorbent sheet" refers to the sheet of absorbent material in the unfolded state, while the term "absorbent sheet product" refers to the folded product resulting from the folding of an absorbent sheet.

In a non-limiting embodiment, the folded absorbent sheet products include single ply or multiple plies paper napkins having a basis weight ranging from about 8 to 35 pounds (lbs) per 3000 square feet.

Figure 1:
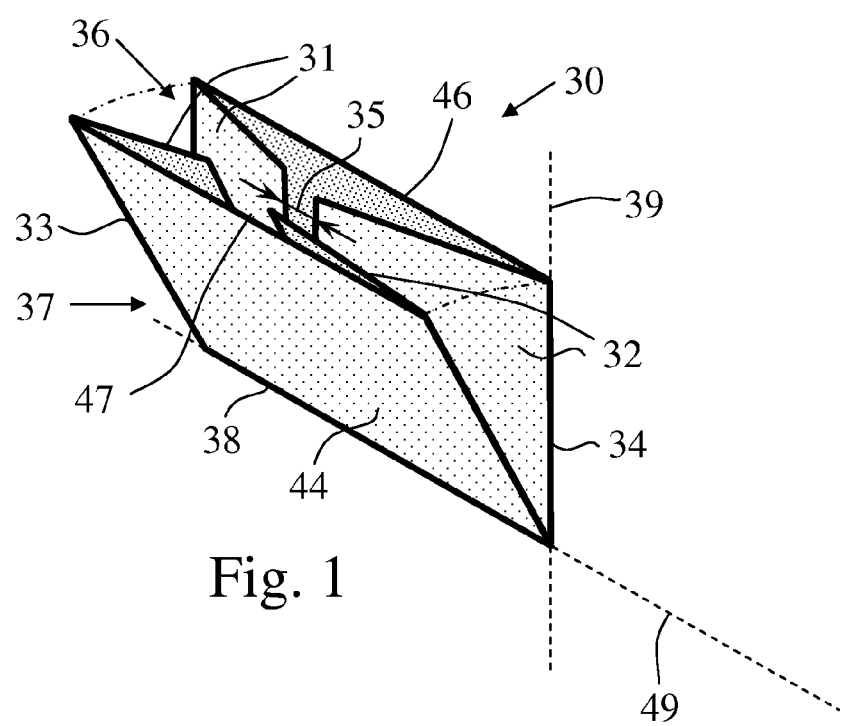
FIG. 1 is a perspective view of an absorbent sheet product in accordance with a first embodiment where the absorbent sheet product has two outer panels of similar length and a gap is provided between a first inner panel and a second inner panel, and shown in a semi-folded configuration.

Referring generally to FIG. 1, there is provided an absorbent sheet product 30 shown in a semi-folded configuration. The absorbent sheet product 30 includes a first folding edge 33 and a second folding edge 34 along a first axis 39. The first folding edge 33 is parallel to the second folding edge 34, but spaced-apart from one another. One skilled in the art will understand that in the context of the present application the term "parallel" should not be interpreted to mean that the first 33 and the second 34 folding edges need to be perfectly parallel to one another. In contrast, one of the folding edges 33, 34 may have a slight angle that diverges from a perfectly parallel configuration.

More particularly, the absorbent sheet is folded along the first 33 and second 34 folding edges in order to form a first inner panel 31 and a second inner panel 32, folded inside the absorbent sheet product 30 in the semi-folded configuration and the folded configuration. The first 31 and second 32 inner panels are folded inwardly towards one another, on a same side of the absorbent sheet product generally referred to as the inner face, thereby resulting in a "C-fold" configuration. The face opposite the inner face is referred to as the outer face. The first 31 and second 32 inner panels result in an increase of the overall volume of the folded absorbent sheet product and in the thickness of the folded absorbent sheet product 30, in the sections covered by the first 31 and second 32 inner panels.

The absorbent sheet product 30 additionally includes a third folding edge 38 perpendicular to the first 33 and second 34 folding edges, along a second axis 49, along which the width of the first and second inner panels is measured. Once again, one skilled in the art will understand that in the context of the present application the term "perpendicular" should not be interpreted to mean that the third folding edge 38 needs to be perfectly perpendicular to the first 33 and the second 34 folding edges. In contrast, the third folding edge may have a slight angle that diverges from a perfectly perpendicular configuration.

The third folding edge 38 divides the absorbent sheet product 30 into two sections forming a first outer panel 36 and a second outer panel 37. Each one of the first 36 and second 37 outer panels comprises a section of the first 31 and second 32 inner panels on one side and a continuous flat face 44 on the other side. The absorbent sheet product 30 is folded along the third folding edge 38 such that the sections of the inner panels 31, 32 face inward, and that the continuous flat faces 44 of the first 36 and second 37 outer panels 36 face outward. In other words, when the outer panels 36, 37 are folded, a section of the first 31 and second 32 inner panels of the first outer panel 36 faces a respective section of the first 31 and second 32 inner panels of the second outer panel 37.

Folding along the third folding edge 38 additionally increases the volume and thickness of the folded absorbent sheet product 30, as the third folding edge 38 provides double folding of the first folding edge 33 and of the second folding edge 34. In other words, along sections thereof, the thickness of folded absorbent sheet product 30 is four times the thickness of the unfolded absorbent sheet product 30.

In the embodiment shown in FIG. 1, a gap 35 is provided between the first inner panel 31 and the second inner panel 32, i.e. free outer edges of the first 31 and second 32 inner panels are spaced-apart from one another. The free outer edges are the edges of the original unfold absorbent sheet extending along the axis 39 which are brought inwardly by the inward folding of the first and second inner panels. The width of the gap 35 can be varied. Such a configuration of the first 31 and second 32 inner panels provides a partial additional layer of absorbent sheet product 30 thus increasing thickness, volume and absorbency of the folded absorbent sheet product 30.

However, one skilled in the art will appreciate that several alternative embodiments are foreseen.

In a first alternative embodiment (not shown), the first inner panel 31 and second inner panel 32 may also have no gap 35 between them, i.e. the free outer edges of the first 31 and second 32 inner panels are contiguous, both free outer edges sharing a common border. For this purpose the first inner panel 31 may be configured to meet the second inner panel 32 at an interface of the two panels. Such configuration of the first panel 31 and second panel 32 provides an additional continuous layer of absorbent sheet product 30, thus also further increasing thickness of the folded absorbent sheet product 30.

Figure 2:
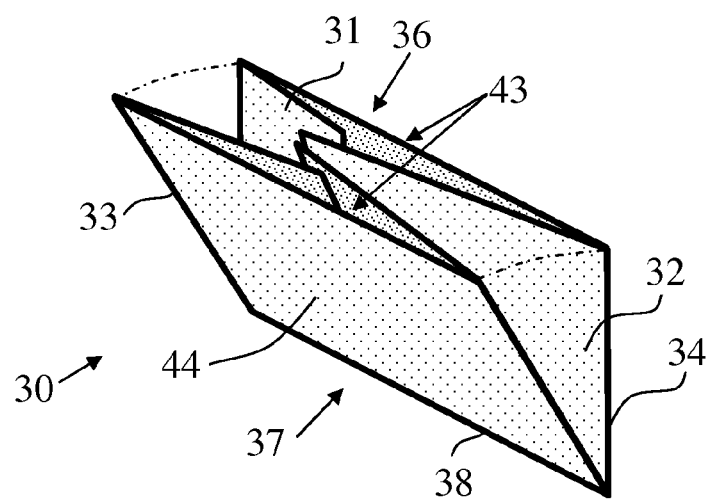
FIG. 2 is a perspective view of the absorbent sheet product, in accordance with an alternative embodiment where the outer panels are of similar length and the inner panels overlap partially, and shown in a semi-folded configuration.
Figure 3:
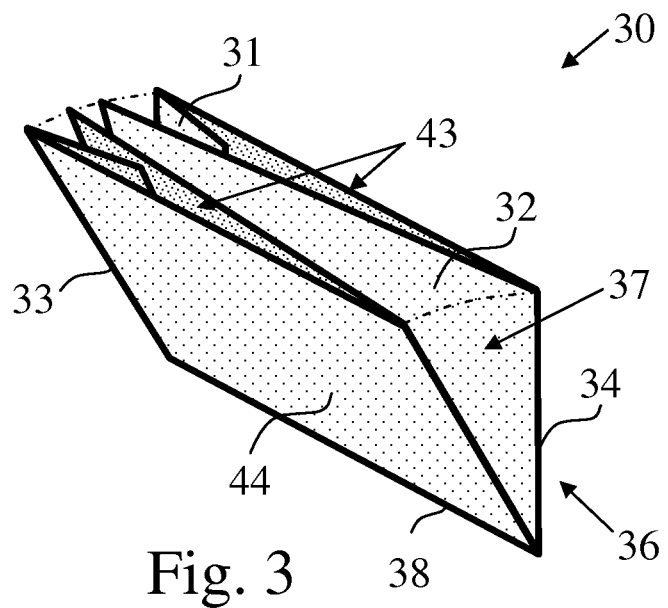
FIG. 3 is a perspective view of the absorbent sheet product, in accordance with an alternative embodiment where the outer panels are of similar length and an outer edge of the second inner panel is contiguous with a first folding edge of the first inner panel, and shown in a semi-folded configuration.
Figure 4:
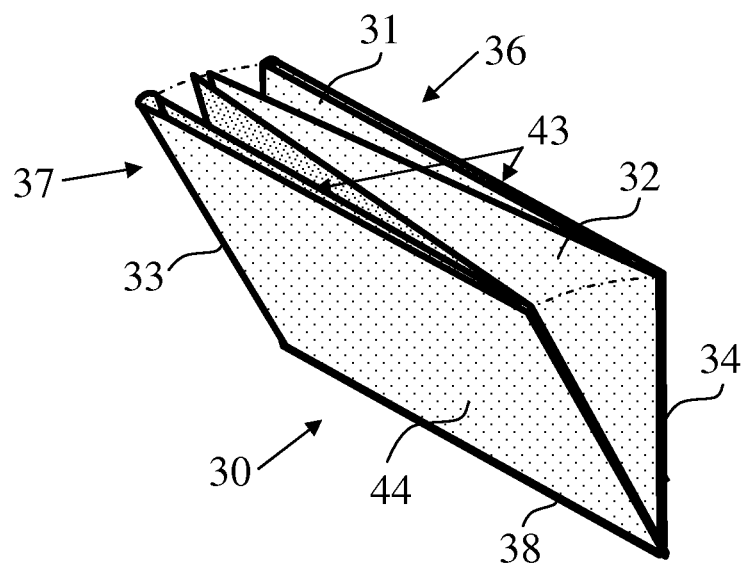
FIG. 4 is a perspective view of the absorbent sheet product, in accordance with an alternative embodiment where the outer panels are of similar length and the inner panels overlap entirely, and shown in a semi-folded configuration.
Figure 5:
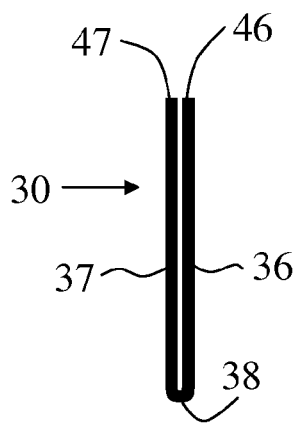
FIG. 5 is a side view of the absorbent sheet products shown in FIGS. 1 to 4, and shown in a folded configuration.

For instance, FIGS. 2 to 4 show alternative embodiments to the folding shown in FIG. 1 wherein the first 31 and second 32 inner panels present different configurations.

Referring now to FIGS. 2 to 3, in an embodiment the first 31 and second 32 inner panels can be configured such that they overlap partially (as shown in FIG. 2), i.e. a section of one of the first 31 and second 32 inner panels extend over the other one of the first 31 and second 32 inner panels. Alternatively, in the embodiment shown in FIG. 3, the first 31 and second 32 inner panels are configured such that the second inner panel 32 overlaps the entire first inner panel 31, while the first inner panel 31 overlaps the second inner panel 32 only partially. In the embodiment shown in FIG. 3, the second inner panel 32 extends from the second folding edge 34 to the first folding edge 33, the free outer edge of the second inner panel 32 being contiguous to the first folding edge 33. One skilled in the art will understand that, in an alternative embodiment (not shown), the free outer edge of the second inner panel 32 can extend beyond the first folding edge 33, i.e. the second inner panel 32 extends past the first inner panel 31. Moreover, it will be apparent to one skilled in the art that the first and second panel could be inverted such that the first inner panel 31 overlaps the entire second inner panel 32, while the second inner panel 32 overlaps the first inner panel 31 only partially. Such a configuration of the first inner panel 31 and second inner panel 32 provides additional partial layers of absorbent sheet product 30, thus increasing the thickness and volume of the folded absorbent sheet product 30.

Now referring to the embodiment shown in FIG. 4, the first 31 and second 32 inner panels can be configured such that they overlap each other entirely. In this embodiment, the first inner panel 31 extends from the first folding edge 33 to the second folding edge 34 and the second inner panel 32 extends from the second folding edge 34 to the first folding edge 33. One skilled in the art will understand that the first 31 or second 32 inner panels could alternatively extend beyond the opposite folding edge, depending on which inner panel is folded over the other. For example, if the second inner panel 32 is folded over the first inner panel 31, it would be possible for the second inner panel 32 to extend beyond the first folding edge 33, while if the first inner panel 31 is folded over the second inner panel 32, it would be possible for the first inner panel 31 to extend beyond the second folding edge 34. Such a configuration of the first inner panel 31 and the second inner panel 32 provides two additional layers of absorbent sheet product 30, thus even further increasing the thickness and volume of the folded absorbent sheet product 30.

Whenever the first 31 and second 32 inner panels overlap at least partially, the folded absorbent sheet product 30 comprises two inside pockets 43 between the overlapping inner panels 31, 32 and the continuous flat face 44. The inside pockets may be suitable for insertion and holding of small objects, such as, without being limitative flatware (forks, knifes, spoons), placement cards, menu cards, wedding gifts or the like.

In the embodiments shown in FIGS. 1 to 5, the third folding edge bisects the absorbent sheet product 30 into two sections of a substantially similar length defined about the first axis 39. This results in the top edges 46, 47 of the outer panels 36 and 37 being contiguous. However, as it will be detailed below, one skilled in the art will appreciate that in alternative embodiments, a gap can be provided between the top edges 46, 47 of the outer panels 36 and 37.

More particularly, referring to FIGS. 7 to 11, there is shown alternative embodiments wherein the third folding edge 38 divides the absorbent sheet product 30 into two outer panels 36, 37 of different lengths. Different lengths of the first 36 and second 37 outer panels result in the top edges 46, 47 of the outer panels 36, 37 being distal from one another and a gap 41 is provided between the two top edges 46, 47. Once again, one skilled in the art will appreciate that the relative length of the two outer panels 36, 37 can vary.

Figure 7:
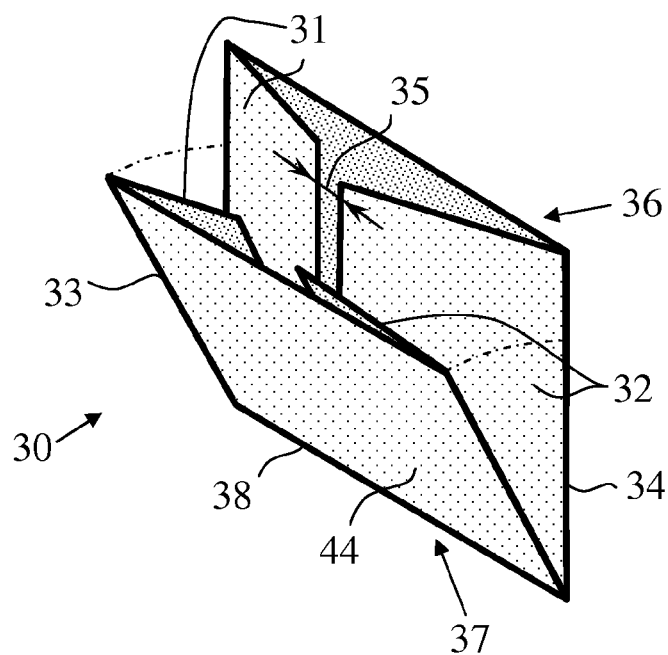
FIG. 7 is a perspective view of the absorbent sheet product, in accordance with an alternative embodiment where the outer panels are of different lengths and a gap is provided between the inner panels, and shown in a semi-folded configuration.
Figure 8:
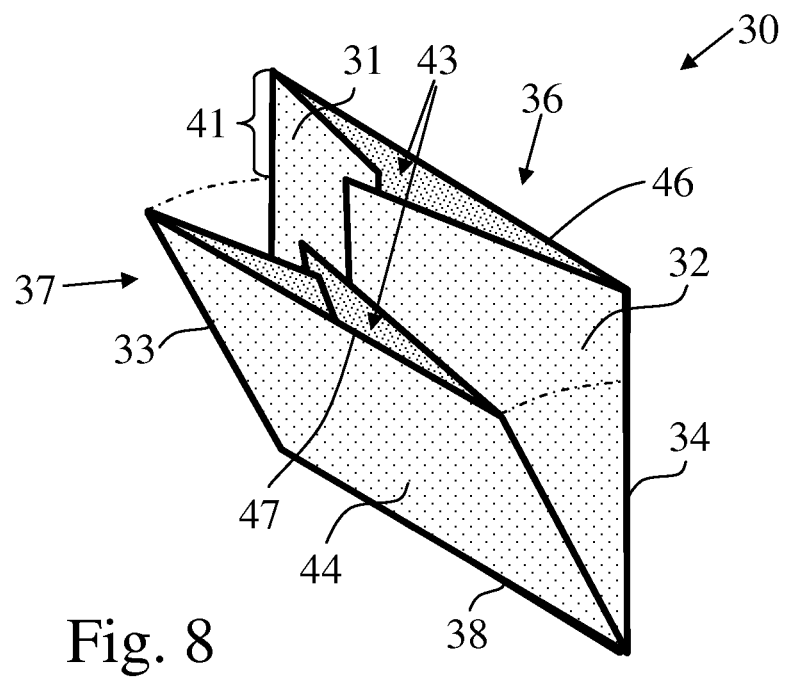
FIG. 8 is a perspective view of the absorbent sheet product, in accordance with an alternative embodiment where the outer panels are of different lengths and the inner panels overlap partially, and shown in a semi-folded configuration.
Figure 9:
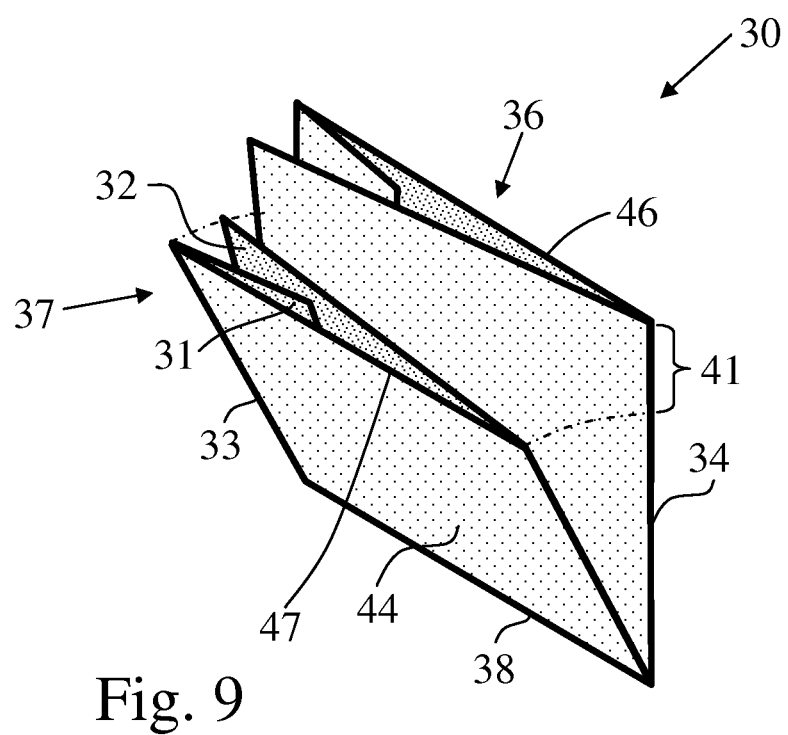
FIG. 9 is a perspective view of the absorbent sheet product, in accordance with an alternative embodiment where the outer panels are of different lengths and an outer edge of the second inner panel is contiguous with a first folding edge of the first inner panel, and shown in a semi-folded configuration.
Figure 10:
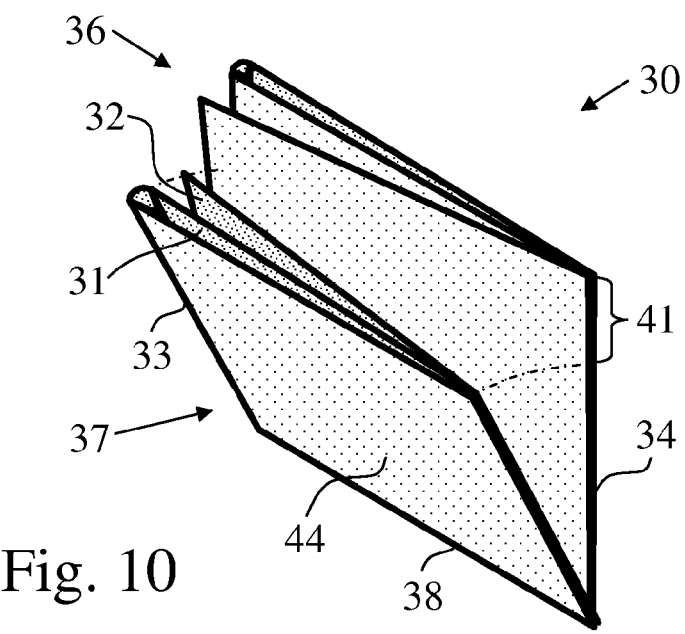
FIG. 10 is a perspective view of the absorbent sheet product, in accordance with an alternative embodiment where the outer panels are of different lengths and the inner panels overlap entirely, and shown in a semi-folded configuration.
Figure 11:
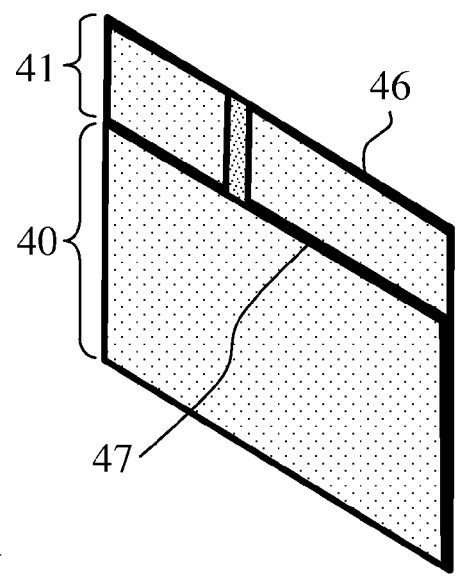
FIG. 11 is a perspective view of the absorbent sheet product of FIG. 7, shown in a folded configuration.
Figure 12:
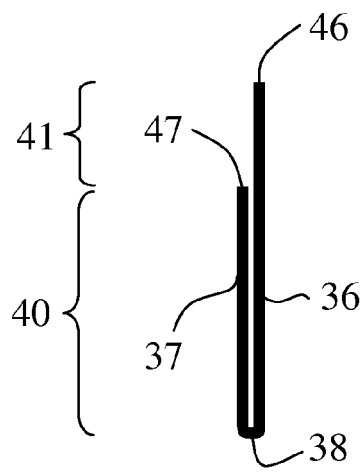
FIG. 12 is a side view of the folded absorbent sheet products of FIGS. 7 to 10, and shown in a folded configuration.
Figure 13:
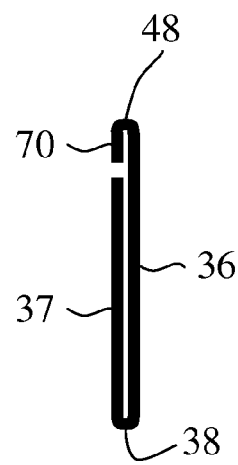
FIG. 13 is a side view of the absorbent sheet product in accordance with an alternative embodiment wherein the absorbent sheet product has a third outer panel folded towards a second one of the outer panels, such that a gap is provided between the second outer panel and the third outer panel, and shown in a folded configuration.
Figure 14:
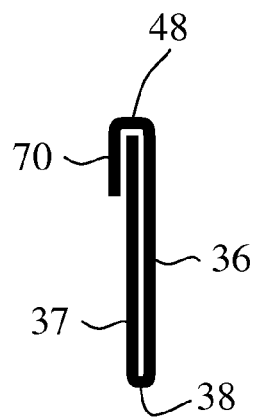
FIG. 14 is a side view of the absorbent sheet product in accordance with an alternative embodiment wherein the third outer panel is folded over the second outer panel, such that the third outer panel partially overlaps the second outer panel, and shown in a folded configuration.
Figure 15:
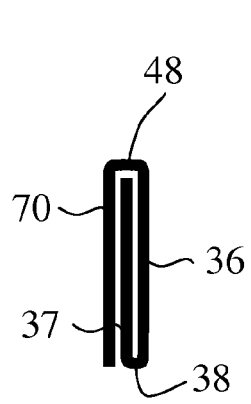
FIG. 15 is a side view of the absorbent sheet product in accordance with an alternative embodiment wherein the third outer panel is folded over the second outer panel, such that the third outer panel entirely overlaps the second outer panel, and shown in a folded configuration.
Figure 16:
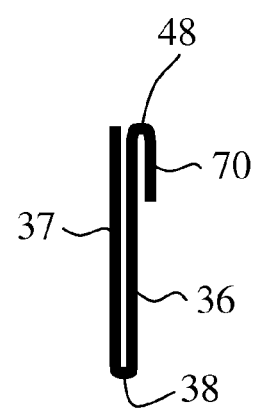
FIG. 16 is a side view of the absorbent sheet product in accordance with an alternative embodiment wherein the third outer panel is folded towards a first one of the outer panels such that the third outer panel partially overlaps the first outer panel, and shown in a folded configuration.

FIGS. 7 to 11 present alternative embodiments where the configuration of the first 31 and second 32 inner panels correspond to the above described embodiment, but where the position of the third folding edge 28 is selected to provide first 36 and second 37 outer panels with different lengths. FIGS. 7 and 11 present an embodiment where the first 31 and second 32 inner panels are configured with a gap 35 in between. FIGS. 8 and 9 present an embodiment where the first 31 and second 32 inner panels are configured to overlap at least partially and FIG. 10 presents an embodiment where the first 31 and second 32 inner panels are configured to overlap entirely. All of the above-mentioned variations concerning the possible configurations of the first 31 and second 32 inner panels apply to the embodiments where the outer panels 36, 37 are of different or similar lengths.

It will be understood that the thickness and volume of the folded absorbent sheet product 30 will be greater in the section 40 where the outer panels 36, 37 overlap, than in the section 41 above the top edge 47 of the shorter outer panel 37, where only a portion of the outer panel 36 having the greater length extends. Consequently, the section 40 where the outer panels 36, 37 overlap, will be referred hereinafter as the section of greater thickness, and the section, above the top edge 47 of the shorter outer panel 37, where only a portion of the outer panel 36 having the greater length extends, will be referred hereinafter as the section 41 of lesser thickness. One skilled in the art, will easily understand that even though, in the illustrated embodiment, the first outer panel 36 is the outer panel having the greater length, in alternative embodiments, the second outer panel 37 could be the panel having the greater length.

Now referring to FIGS. 13 to 17, there is shown alternative embodiments wherein the folded absorbent sheet product 30 is provided with a fourth folding edge 48 perpendicular to the first 33 and second 34 folding edges, i.e. it extends substantially parallel to the second axis 49. Once again, one skilled in the art will understand that in the context of the present application the term "perpendicular" should not be interpreted to mean that the fourth folding edge 48 needs to be perfectly perpendicular to the first 33 and the second 34 folding edges, and that the fourth folding edge 48 may have a slight angle that diverge from a perfectly perpendicular configuration. One skilled in the art will also understand that the perpendicularity of the fourth folding edge 48 with the first 33 and second 34 folding edge results in the fourth folding edge being parallel to the third folding edge.

The fourth folding edge 48 forms a third outer panel 70 into the section of lesser thickness 41. As can be seen in the embodiments shown in FIGS. 13 to 17, the third outer panel 70 is folded towards the outer panel of shorter length 37 in a spaced-apart configuration (embodiment shown in FIG. 13), a partial overlapping configuration (embodiment shown in FIG. 14) or a complete overlapping configuration (embodiment shown in FIG. 15). In the embodiments shown in FIGS. 14 and 15, the fourth folding edge 48 is substantially contiguous to the top edge 47 of the shorter outer panel 37. However, one skilled in the art will appreciate that the position of the fourth folding edge 48 along the section of lesser thickness 41 can vary. Similarly, in the embodiment shown in FIG. 13, the position of the fourth folding edge 48 along the section of lesser thickness 41 can also vary.

Figure 17:
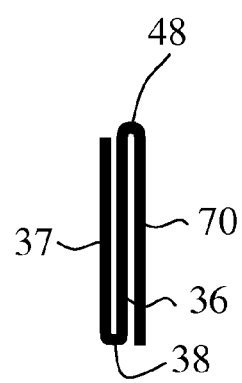
FIG. 17 is a side view of the absorbent sheet product in accordance with an alternative embodiment wherein the third outer panel is folded towards the first outer panel such that the third outer panel entirely overlaps the first outer panel, and shown in a folded configuration.

In other possible embodiments, the third outer panel 70 may be folded towards the outer panel of greater length 36 in a partial overlapping configuration (embodiment shown in FIG. 16) or a complete overlapping configuration (embodiment shown in FIG. 17). The third outer panel 70 uses the section of lesser thickness 41 to either increase the volume and thickness of the folded absorbent sheet product 30 in a particular section thereof or to increase the volume and thickness of the overall folded absorbent sheet product 30. Once again, one skilled in the art will easily understand that even though, in the illustrated embodiments, the first outer panel 36 is the outer panel having the greater length, in alternative embodiments, the second outer panel 37 could be the panel having the greater length. Alternatively, the third outer panel 70 could also be formed outside of the section of lesser thickness 41 (i.e. in the section 40 where the first and the second outer panels 36, 37 overlap), in the outer panel of greater length or the outer panel of lesser length. In another alternative embodiment, multiples additional panels could also be formed.

In an embodiment a plurality of folded absorbent sheet products 30 such as the ones described in the above-described embodiments may be stacked onto one another to form a stack 50.

Figure 6:
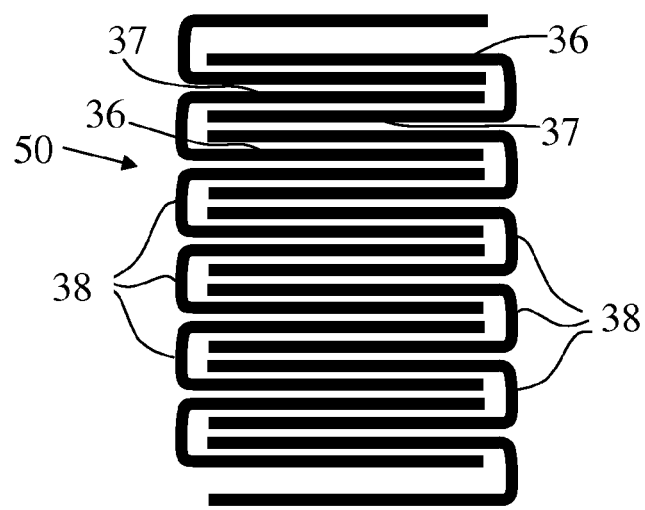
FIG. 6 is a side view of a stack of a plurality of the folded absorbent sheet products shown in FIGS. 1 to 4, in accordance with an embodiment wherein the absorbent sheet products are stacked in an interfolded configuration.

Now referring to FIG. 6, a stack 50 of absorbent sheet products 30 having outer panels of a similar length is shown. The stack 50 is formed of a plurality of absorbent sheet products 30 being stacked onto one another in an interfold configuration, i.e. at each fold an outer panel of the previous sheet and an outer panel of the next sheet engage with each other. This way, when drawing a sheet from the package, a panel of the next sheet protrudes with subsequent practical employment for certain types of users. Interfolded sheets, such as, and without being limitative, napkins, are sheets of materials arranged in a stack of superposed sheets which are each folded at least once. The sheets are interlinked in such a way that the separate folded sheets of material form a chain of sheets where each sheet has a leading panel and a trailing panel, the trailing panel being at least partly overlapped with the leading panel of the subsequent sheet in the stack. In this manner, the individual sheets are held loosely together by means of frictional forces arising between the overlapping parts. The sheets may be dispensed from a dispenser by pulling at the leading panel of the first sheet in the stack. In this manner, the first material sheet is extracted at the same time as a predetermined part of the leading panel of a subsequent material sheet is fed into a dispensing position in the dispenser.

In the embodiment shown in FIG. 6, the interfold configuration of the stack 50 is provided by the first outer panel 36 of one absorbent sheet product 30 being located between the first 36 and second 37 outer panels of each corresponding adjacent absorbent sheet product 30 of the stack 50. In other words, unless the absorbent sheet product is at the top or the bottom of the stack, it has a first outer panel 36 located between the first 36 and second 37 outer panels of an adjacent absorbent sheet product 30 located immediately above it in the stack, and a second outer panel 37 located between the first 36 and second 37 outer panels of an adjacent absorbent sheet product 30 located immediately below it in the stack, or vice-versa. The top and bottom absorbent sheet products 30 of the stack 50 only present one outer panel interfolded with the adjacent absorbent sheet product 30 located immediately below (in the case of the absorbent sheet product 30 located on top of the stack) and the adjacent absorbent sheet product 30 located immediately above (in the case of the absorbent sheet product 30 located at the bottom of the stack). Moreover, the third folding edge 38 of each adjacent absorbent sheet product 30 of the stack 50 faces a direction opposite that of the absorbent sheet product 30 located immediately above and below.

Figure 22:
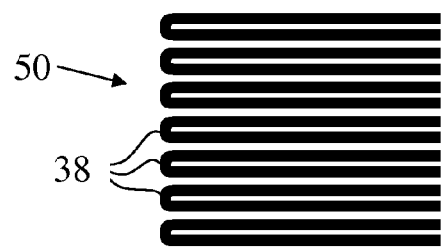
FIG. 22 is a side view of a stack of a plurality of the folded absorbent sheet products of FIGS. 1 to 5, in accordance with an embodiment wherein the absorbent sheet products are stacked one over the other.

FIG. 22 shows a stack 50 of absorbent sheet products 30 having outer panels of similar lengths, and simply stacked on top of each other. In the illustrated embodiment, the absorbent sheet products 30 are stacked with their third folding edge 38 facing the same direction. However one skilled in the art will easily understand that other embodiments where the third folding edge 38 of the absorbent sheet products 30 face opposite direction alternatively, or according to any other pattern thereof, could be provided.

Figure 18:
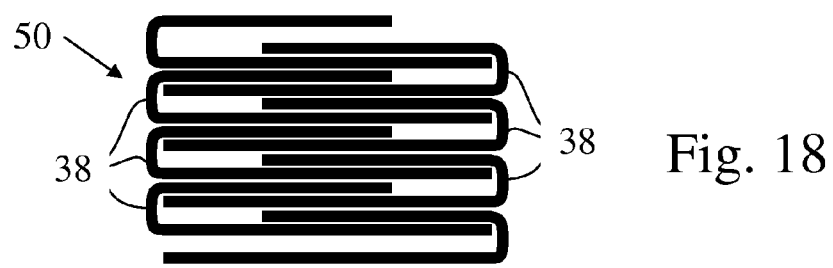
FIG. 18 is a side view of a stack of a plurality of the folded absorbent sheet products shown in FIGS. 7 to 10, in accordance with an embodiment where the outer panel of greater length is upward and the outer panel of lesser length is downward.
Figure 19:
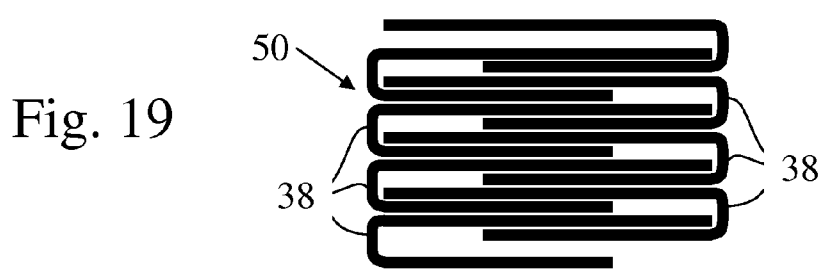
FIG. 19 is a side view of a stack of a plurality of the folded absorbent sheet products shown in FIGS. 7 to 10, in accordance with an embodiment where the outer panel of lesser length is upward and the outer panel of greater length is downward.
Figure 20:
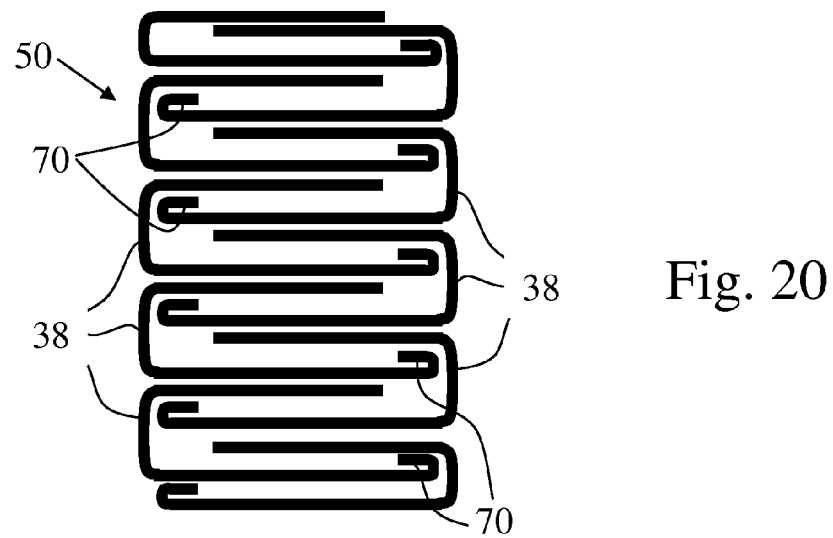
FIG. 20 is a side view of a stack of a plurality of the folded absorbent sheet product shown in FIG. 13, in accordance with an embodiment wherein the absorbent sheet products are stacked in an interfolded configuration.
Figure 21:
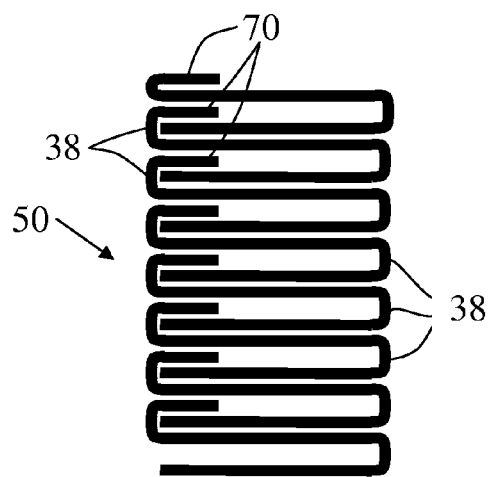
FIG. 21 is a side view of a stack of a plurality of the folded absorbent sheet product shown in FIG. 16, in accordance with an embodiment wherein the absorbent sheet products are stacked in an interfolded configuration.

Now referring to FIGS. 18 to 21, in alternative embodiments, a plurality of absorbent sheet products 30 having outer panels of different lengths may also be stacked into a stack 50, in an interfold configuration. As can be seen in the embodiments illustrated in FIGS. 18 and 19, the absorbent sheet products 30 having outer panels of different lengths may be stacked in an interfold configuration with the outer panel of lesser length on top (as shown in FIG. 18) or at the bottom (as shown in FIG. 19). In embodiments where an a third outer panel 70 is provided, the absorbent sheet products 30 may be stacked in an interfold configuration with the third outer panel 70 on top (as shown in FIG. 21) or at the bottom (as shown in FIG. 20). One skilled in the art will understand that any configuration of absorbent sheet products 30 with a third outer panel 70 may be stacked in an interfold configuration and that interfolded stacking is not limited to the illustrated configurations of stacks of absorbent sheet products 30. Moreover, it will be understood that even though in the illustrated embodiments, the absorbent sheet products 30 are stacked with the outer panel of lesser length, or the third outer panel 70, always at the top or the bottom, in alternative embodiment, the positioning of the outer panel of lesser length, or the third outer panel 70, may alternate according to any predefined sequence.

Figure 23:
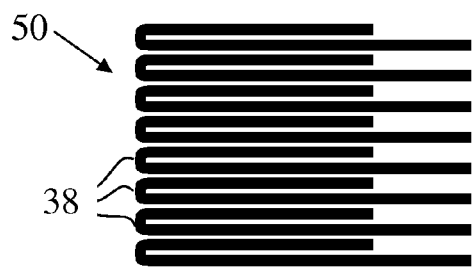
FIG. 23 is a side view of a stack of a plurality of the folded absorbent sheet products of FIGS. 7 to 12, in accordance with an embodiment wherein the absorbent sheet products are stacked one over the other, the outer panel of lesser length being upward and the outer panel of greater length being downward.
Figure 24:
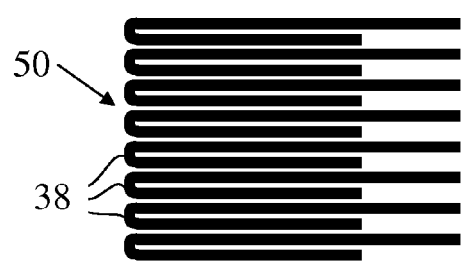
FIG. 24 is a side view of a stack of a plurality of the folded absorbent sheet products of FIGS. 7 to 12, in accordance with an embodiment wherein the absorbent sheet products are stacked one over the other, the outer panel of greater length being upward and the outer panel of lesser length being downward.

Each one of FIGS. 23 and 24 show a stack 50 of absorbent sheet products 30 having outer panels of different lengths, and simply stacked on top of each other. In the embodiment of FIG. 23, the absorbent sheet products 30 are stacked with the outer panel of lesser length upward and the outer panel of greater length downward. In contrast, in the embodiment of FIG. 24, the absorbent sheet products 30 are stacked with the outer panel of lesser length downward and the outer panel of greater length upward. Once again, even though in the illustrated embodiment the absorbent sheet products 30 are stacked with their third folding edge 38 facing the same direction, one skilled in the art will understand that other embodiments where the third folding edge 38 of the absorbent sheet products 30 face opposite direction alternatively, or according to any other pattern thereof, could be provided.

It will be understood that in the above described interfolded stack, each outer panel that is interfolded between the first and second outer panel of an adjacent absorbent sheet product 30 need not be completely inserted therein, i.e. until a top edge 46 or 47 reaches the third folding edge 38 of the adjacent absorbent sheet products 30, and that only a section of the outer panel that is interfolded between the first and second outer panel of an adjacent absorbent sheet product 30 may be inserted therein.

There is provided a method for folding and stacking absorbent sheet products 30 in order to achieve the above-described stacked and folded configurations.

Referring to FIG. 1, the method of folding the absorbent sheet product 30 comprises folding the absorbent sheet product 30 inwardly, along a first folding line corresponding to the first folding edge 33, to form a first inner panel 31. The method also comprises folding the absorbent sheet product 30 inwardly, along a second folding line corresponding to the second folding edge 34, to form a second inner panel 32. The first and second folding lines are substantially parallel to one another. The method may also comprise folding the absorbent sheet product 30 along a third folding line corresponding to the third folding edge 38. The third folding line is perpendicular to the first and second folding lines and forms a first outer panel and a second outer panel. When an absorbent sheet product 30 is folded according to the present method, a section of the inner panels 31, 32 of the first outer panel 36 faces a section of the inner panels, 31, 32 of the second outer panel 37.

The method of folding the absorbent sheet product 30, may also comprise configuring the first and second folding line, such that the first 31 and second 32 inner panels are provided with a gap in between (as shown in FIG. 1), partially overlap each other (as shown in FIG. 2), entirely overlap each other (as shown in FIG. 4) or such that the first inner panel 31 completely overlaps the second inner panel 32, while the second inner panel 32 partially overlaps the first inner panel 31 (as shown in FIG. 3).

The method of folding the absorbent sheet product 30, may also comprise configuring the third folding line, such that the first 36 and second 37 outer panels are of a similar height (as shown in FIGS. 1 to 5) or of different heights (as shown in FIGS. 7 to 12).

The method of folding the absorbent sheet product 30 may also comprise folding the absorbent sheet along a fourth folding line corresponding to the fourth folding edge 48. The fourth folding line is perpendicular to the first and second folding lines and forms a third outer panel 70. In an embodiment, the fourth folding line is provided on the outer panel of greater length; however one skilled in the art will understand that alternatively it could be provided on the outer panel of lesser length.

Subsequent to the folding of the absorbent sheet products 30, the method of stacking the absorbent sheet products 30 comprises stacking a plurality of absorbent sheet products 30 either simply on top of one another (as shown on FIGS. 22 to 24) or in an interfold configuration (as shown in FIGS. 6 and 18 to 21). When the absorbent sheet products 30 are stacked in an interfold configuration, the method comprises interfolding at least a section of one of the outer panels 36, 37 of an absorbent sheet product 30 between the first 36 and second 37 outer panels of each corresponding adjacent absorbent sheet product 30 of the stack 50.

It will be understood that all of the above mentioned variants concerning the possible embodiments of the absorbent sheet products 30 and the stack 50 apply to the method of folding and stacking the absorbent sheet products 30. It will be appreciated that the methods described herein may be performed in the described order, or in any suitable order.

Several alternative embodiments and examples have been described and illustrated herein. The embodiments of the invention described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the scope of the invention as defined in the appended claims.

The invention claimed is:

1. A stack of interfolded absorbent sheet products comprising a plurality of absorbent sheets having an inner face and an opposed outer face, each of the absorbent sheets comprising:
    a first folding edge and a second folding edge extending substantially parallel to one another along a first axis and defining respectively a first inner panel and a second inner panel, each of the absorbent sheets being folded inwardly along the first and the second folding edges towards the inner face with the first inner panel and the second inner panel being folded towards one another, each of the absorbent sheets being unfolded along the first axis between the first folding edge and the second folding edge; and
    a third folding edge extending substantially perpendicular to the first and the second folding edges, bisecting each of the absorbent sheets, and defining a first outer panel and a second outer panel, each of the absorbent sheets being folded along the third folding edge such that the first and the second inner panels are inwardly facing;
wherein at least one of the first and the second outer panels is at least partially inserted between the first and the second outer panels of an adjacent one of the absorbent sheet products of the stack.

2. The stack of interfolded absorbent sheet products of claim 1, wherein the first and the second folding edges are configured to provide a gap between the first and the second inner panels.

3. The stack of interfolded absorbent sheet products of claim 1, wherein each one of the first and the second inner panels comprises a free outer edge and the free outer edges of the first and the second inner panels are contiguous to one another when folded inwardly along the first and the second folding edges.

4. The stack of interfolded absorbent sheet products of claim 1, wherein the first and the second inner panels at least partially overlap when folded inwardly along the first and the second folding edges.

5. The stack of absorbent sheet products of claim 1, wherein a free outer edge of the second inner panel is contiguous to the first folding edge.

6. The stack of interfolded absorbent sheet product of claim 5, wherein the first inner panel comprises a free outer edge, the free outer edge of the first panel being contiguous to the second folding edge or extending past the second inner panel.

7. A stack of interfolded absorbent sheet products comprising a plurality of absorbent sheets, each one of the absorbent sheets being folded twice about a first axis to define two inwardly folded inner panels folded respectively along a first folding edge and a second folding edge, and at least once about a second axis, substantially perpendicular to the first axis, to define at least two outer panels sandwiching the inner panels therebetween and wherein the at least two outer panels comprise a first outer panel and a second outer panel separated by a third folding edge bisecting each one of the absorbent sheets, the first folding edge and the second folding edge being spaced-apart from one another along the second axis and each of the absorbent sheets being unfolded along the first axis between the first folding edge and the second folding edge, wherein each of the absorbent sheet products comprises at least one of the outer panels at least partially sandwiched between a pair of the outer panels of an adjacent one of the absorbent sheet products of the stack, wherein each one of the absorbent sheet products is entirely detached from all other absorbent sheet products of the stack.

8. The stack of interfolded absorbent sheet products of claim 7, wherein the inwardly folded inner panels extend substantially parallel to one another.

9. The stack of interfolded absorbent sheet products of claim 7, wherein the inwardly folded inner panels are spaced-apart from one another to define a gap therebetween.

10. The stack of interfolded absorbent sheet products of claim 7, wherein each of the inwardly folded inner panels has an outer edge and the outer edges of the inwardly folded inner panels are contiguous to one another.

11. The stack of interfolded absorbent sheet products of claim 7, wherein the inwardly folded inner panels are at least partially superposed.

12. The stack of interfolded absorbent sheet products of claim 7, wherein a first one of the inwardly folded inner panels is superposed to a second one of the inwardly folded inner panels along an entire width thereof.

13. The stack of interfolded absorbent sheet products of claim 12, wherein a first one of the inner panels is folded inwardly along a first folding edge and a free outer edge of a second one of the inner panels is substantially contiguous to the first folding edge.

14. The stack of interfolded absorbent sheet products of claim 13, wherein the second inner panel is folded inwardly along a second folding edge and a free outer edge of the first inner panel is substantially contiguous to the second folding edge.

15. The stack of interfolded absorbent sheet products of claim 7, wherein each one of the absorbent sheets is folded twice about the second axis to define a third outer panel.

16. The stack of interfolded absorbent sheet products of claim 7, wherein each one of the absorbent sheets comprises at least six panels separated by folding edges extending along one of the first and the second axes.

17. A stack of interfolded absorbent sheet products comprising a plurality of absorbent sheets having an inner face and an opposed outer face, each of the absorbent sheets comprising:
    a first folding edge and a second folding edge extending substantially parallel to one another along a first axis and defining respectively a first inner panel and a second inner panel, each of the absorbent sheets being folded inwardly along the first and the second folding edges towards the inner face with the first inner panel and the second inner panel being folded towards one another, each of the absorbent sheets being unfolded along the first axis between the first folding edge and the second folding edge; and a third folding edge extending substantially perpendicular to the first and the second folding edges and defining a first outer panel and a second outer panel with the first outer panel extending past the second outer panel, each of the absorbent sheets being folded along the third folding edge such that the first and the second inner panels are inwardly facing;

wherein at least one of the first and the second outer panels is at least partially inserted between the first and the second outer panels of an adjacent one of the absorbent sheet products of the stack.

18. The stack of interfolded absorbent sheet products of claim 17, wherein each of the absorbent sheets further comprises a fourth folding edge defined in the first outer panel and extending substantially parallel to the third folding edge, the absorbent sheets being folded along the fourth folding edge to define a third outer panel.

19. The stack of interfolded absorbent sheet products of claim 17, wherein the first and the second folding edges are configured to provide a gap between the first and the second inner panels.

20. The stack of interfolded absorbent sheet products of claim 17, wherein each one of the first and the second inner panels comprises a free outer edge and the free outer edges of the first and the second inner panels are contiguous to one another when folded inwardly along the first and the second folding edges.

21. The stack of interfolded absorbent sheet products of claim 17, wherein the first and the second inner panels at least partially overlap when folded inwardly along the first and the second folding edges.

22. The stack of absorbent sheet products of claim 17, wherein a free outer edge of the second inner panel is contiguous to the first folding edge.

23. The stack of interfolded absorbent sheet product of claim 22, wherein the first inner panel comprises a free outer edge, the free outer edge of the first panel being contiguous to the second folding edge or extending past the second inner panel.

24. A stack of interfolded absorbent sheet products comprising a plurality of absorbent sheets, each one of the absorbent sheets being folded twice about a first axis to define two inwardly folded inner panels folded respectively along a first folding edge and a second folding edge, and at least once about a second axis, substantially perpendicular to the first axis, to define at least two outer panels sandwiching the inner panels therebetween, the at least two outer panels comprise a first outer panel and a second outer panel with the first outer panel extending past the second outer panel, the first folding edge and the second folding edge being spaced-apart from one another along the second axis and each of the absorbent sheets being unfolded along the first axis between the first folding edge and the second folding edge, wherein each of the absorbent sheet products comprises at least one outer panel at least partially sandwiched between a pair of outer panels of an adjacent one of the absorbent sheet products of the stack, wherein each one of the absorbent sheet products is entirely detached from all other absorbent sheet products of the stack.

25. The stack of interfolded absorbent sheet products of claim 24, wherein the inwardly folded inner panels extend substantially parallel to one another and are spaced-apart from one another to define a gap therebetween.

26. The stack of interfolded absorbent sheet products of claim 24, wherein each of the inwardly folded inner panels has an outer edge and the outer edges of the inwardly folded inner panels are contiguous to one another.

27. The stack of interfolded absorbent sheet products of claim 24, wherein the inwardly folded inner panels extend substantially parallel to one another and are at least partially superposed.

28. The stack of interfolded absorbent sheet products of claim 24, wherein a first one of the inwardly folded inner panels is superposed to a second one of the inwardly folded inner panels along an entire width thereof.

29. The stack of interfolded absorbent sheet products of claim 24, wherein the first outer panel is folded along the second axis to define a third outer panel.

30. A stack of interfolded absorbent sheet products comprising a plurality of absorbent sheets, each one of the absorbent sheets being folded twice about a first axis to define two inwardly folded inner panels folded respectively along a first folding edge and a second folding edge, and at least once about a second axis, substantially perpendicular to the first axis, to define at least two outer panels sandwiching the inner panels therebetween, the first folding edge and the second folding edge being spaced-apart from one another along the second axis and each of the absorbent sheets being unfolded along the first axis between the first folding edge and the second folding edge, wherein each of the absorbent sheet products comprises at least one outer panel at least partially sandwiched between a pair of outer panels of an adjacent one of the absorbent sheet products of the stack, wherein each one of the absorbent sheet products is entirely detached from all other absorbent sheet products of the stack and each one of the absorbent sheets consists of six panels separated by folding edges extending along one of the first and the second axes.

* * * * *